(12) United States Patent
Secora et al.

(10) Patent No.: US 7,837,628 B2
(45) Date of Patent: Nov. 23, 2010

(54) ELECTRO-MECHANICAL SYSTEM FOR ELECTROPHYSIOLOGY AND HEMODYNAMIC STUDIES

(75) Inventors: Gary J. Secora, Menomonee Falls, WI (US); Sachin Vadodaria, Fox Point, WI (US); Richard W. Schefelker, Menomonee Falls, WI (US); Claudio P. Mejia, Wauwatosa, WI (US); Michael McOlash, Wauwatosa, WI (US); Rodger F. Schmit, West Bend, WI (US); Daniel R. Schneidewend, Menomonee Falls, WI (US); James M. Peschke, Harvard, IL (US); Pat T. Moran, New Berlin, WI (US)

(73) Assignee: The General Electric Company, Schenectady, NY (US)

( * ) Notice: Subject to any disclaimer, the term of this patent is extended or adjusted under 35 U.S.C. 154(b) by 1093 days.

(21) Appl. No.: 11/535,200

(22) Filed: Sep. 26, 2006

(65) Prior Publication Data

US 2008/0027417 A1   Jan. 31, 2008

Related U.S. Application Data

(60) Provisional application No. 60/800,447, filed on May 15, 2006.

(51) Int. Cl.
    *A61B 5/02* (2006.01)
(52) U.S. Cl. .................................................... 600/508
(58) Field of Classification Search ..................... 606/1; 356/41; 600/508
    See application file for complete search history.

(56) References Cited

U.S. PATENT DOCUMENTS

| 4,684,245 A * | 8/1987 | Goldring | ..................... 356/41 |
| 2006/0276775 A1 * | 12/2006 | Rosenberg et al. | ............. 606/1 |

* cited by examiner

*Primary Examiner*—George Manuel
(74) *Attorney, Agent, or Firm*—Andrus, Sceales, Starke & Sawall, LLP (57) ABSTRACT

An electrical-mechanical system may be used in electrophysiology and hemodynamic studies. The system may include a mounting arrangement couplable to a support surface for supporting a patient. At least one catheter input module may be electrically and mechanically coupled to the mounting arrangement, the catheter input module being connectable to catheters for use in the patient. A central processing device may be attached to the support surface and placed in communication with the mounting arrangement.

18 Claims, 10 Drawing Sheets

ELECTRO-MECHANICAL SYSTEM FOR ELECTROPHYSIOLOGY AND HEMODYNAMIC STUDIES

CROSS REFERENCE TO RELATED APPLICATION

This application relates to and claims priority from U.S. Provisional Application Ser. No. 60/800,447 filed on May 15, 2006 May 5, 2006.

FIELD OF THE INVENTION

The present invention relates generally to the field of invasive cardiology and, more particularly, pertains to the coupling and positioning of apparatus used in electrophysiology (EP) and hemodynamic (HEMO) studies.

BACKGROUND OF THE INVENTION

EP and HEMO procedures are complex and sensitive procedures wherein significant and critical data relating to electrical signals and pressures of the heart are transmitted from a patient via intracardiac catheters which perform certain sensing and stimulating functions. Typically, data from the catheters is transmitted from a number of wires having input jacks connected to several catheter input modules which are separately located adjacent a patient's bed. Further wires are used to transmit the cardiac data to a relatively large central processing device usually located on the floor of a procedure room.

The nature of such arrangement creates a jungle of wires which not only presents clutter, but also causes electrical noise problems in the transmission of data. Further, the current arrangement used in EP and HEMO procedures prevents a room-to-room portability which would be desirable. Another drawback resides in the fact that one arrangement is required for an EP study, while a different arrangement is required for a HEMO study.

These problems and drawbacks and further related issues are addressed by the system embodying the present invention.

BRIEF DESCRIPTION OF THE INVENTION

In one aspect of the invention, an electromechanical system is used in electrophysiology and hemodynamic studies. The system includes a mounting arrangement coupled to a support surface supporting a patient provided with catheters. At least one catheter input module is electrically and mechanically coupled to the mounting arrangement, the catheter input module being connected to catheters in the patient. A central processing device is attached to the support surface and placed in communication with the mounting arrangement.

The mounting arrangement is removably coupled by a snap fit and slidably supported to the support surface. The mounting arrangement and the catheter input module have cooperating alignment and locking structure. Several catheter input modules are electrically and mechanically coupled to the mounting arrangement in a stacked fashion. The central processing device is coupled to the mounting arrangement by a single cable. The mounting arrangement is extended either above or below the patient's support surface. The mounting arrangement and the catheter input module are locked together by a latching arrangement. The mounting arrangement and the catheter input module are electrically connected together by a harness having a ribbon cable. The catheter input module has a removable cover formed with openings for receiving input jacks attached to the catheters in the patient. The removable cover is provided with an LED arrangement for verifying the electrical coupling of the mounting arrangement to the catheter input module. The mounting arrangement includes a mounting platter rotatably attached to a top end of a vertical spindle, and an offset extension with an attachment bracket fixed to a lower end of the spindle.

The central processing device includes a base attached to the support surface and an acquisition module coupled to the base. The central processing device is used in both electrophysiology and hemodynamic studies. The latching arrangement is formed by a ramped tongue on the catheter input module and a slotted dome on the mounting arrangement. The stacked catheter modules and the mounting arrangement are locked together by a latching arrangement. The stacked catheter input modules and the mounting arrangement are electrically connected together by a harness arrangement. A top surface of the mounting plate is provided with shoes that are aligned with and engaged by feet formed on a bottom surface of the catheter input module. A top surface of the mounting platter is provided with a slotted dome that is aligned with and received in a cored out portion formed on a bottom surface of the catheter input module. Rear surfaces of the mounting platter and the catheter input module are formed with projecting electrical connectors that are coupled together.

In another aspect of the invention, a patient monitoring system is used in electrophysiology and hemodynamic studies of a patient positioned on a support surface and provided with catheters connected to a series of catheter input modules in communication with a central processing device. The invention is improved wherein a mounting arrangement is movably coupled to the support surface. The catheter input modules are electrically and mechanically connected to each other and the mounting arrangement in a stacked formation thereon. The central processing device is removably attached to the support structure and electrically connected to the mounting arrangement by a single cable.

BRIEF DESCRIPTION OF THE DRAWING

The drawings illustrate the best mode presently contemplated of carrying out the invention.

In the drawings.

DETAILED DESCRIPTION

Figure 1:
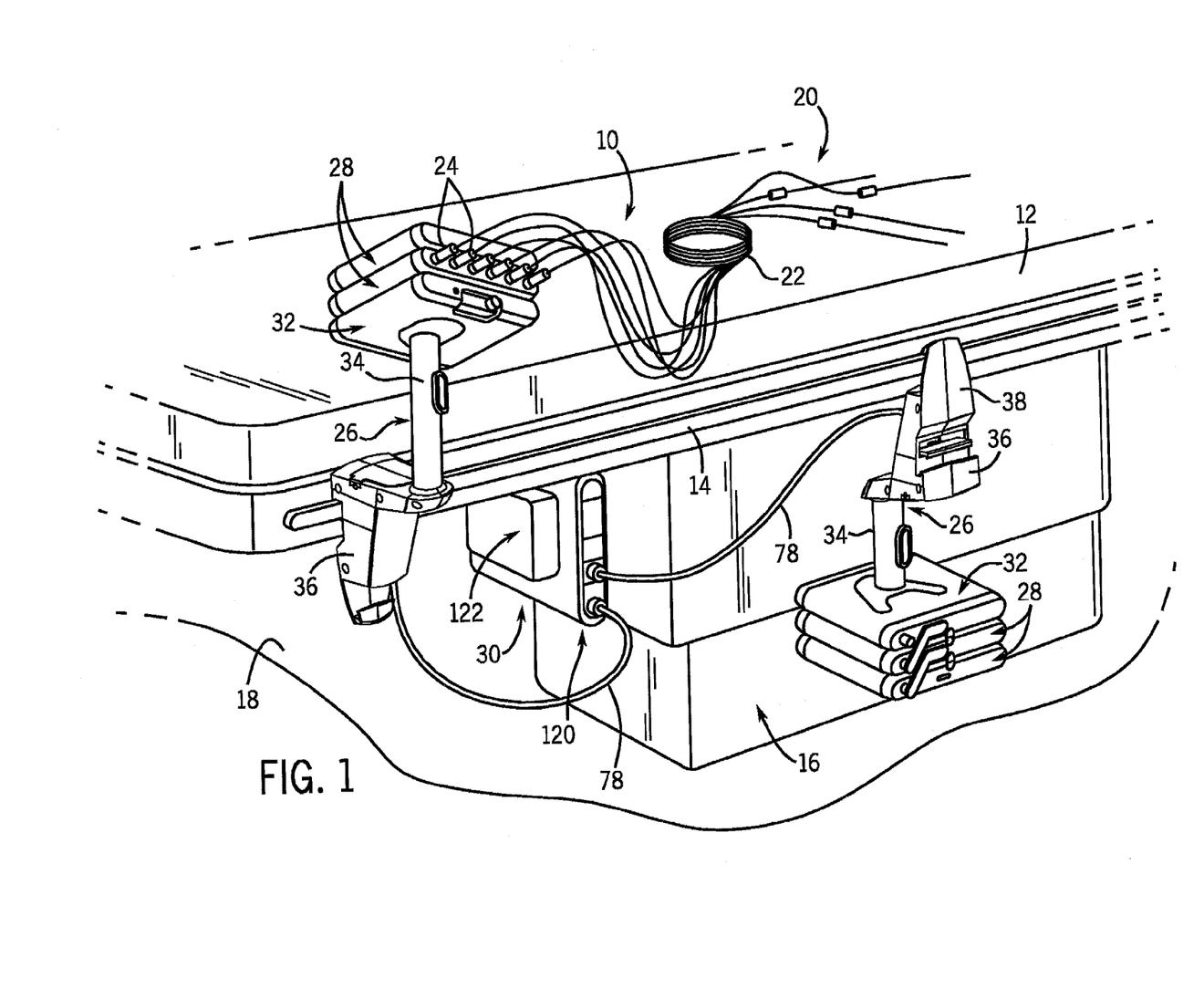
FIG. 1 is a perspective view of an electromechanical system for electrophysiology and hemodynamic studies.

Referring now to the drawings, FIG. 1 illustrates an electro-mechanical system 10 useful in both electrophysiology (EP) and hemodynamic (HEMO) studies of a patient. During the course of such studies, the patient normally lies in a generally horizontally reclined position upon a flat support surface of a patient support structure 12, such as a table or bed. The patient support structure 12 typically includes a structural framework having a pair of side rails (one being seen at 14), and a depending pedestal 16 extending to a floor 18. When positioned on the patient support structure 12, the patient is provided with a series of intracardiac catheters 20 having cables or wires 22 with jacks 24 on distal ends thereof. The patient may further be provided with other items such as external surface sensors, a blood pressure cuff and pressure probes for conducting an ECG and monitoring vital statistics and heart pressures during the studies.

The electromechanical system 10 is comprised of a mounting arrangement 26, at least one catheter input module 28, and a central processing device 30.

Figure 2:
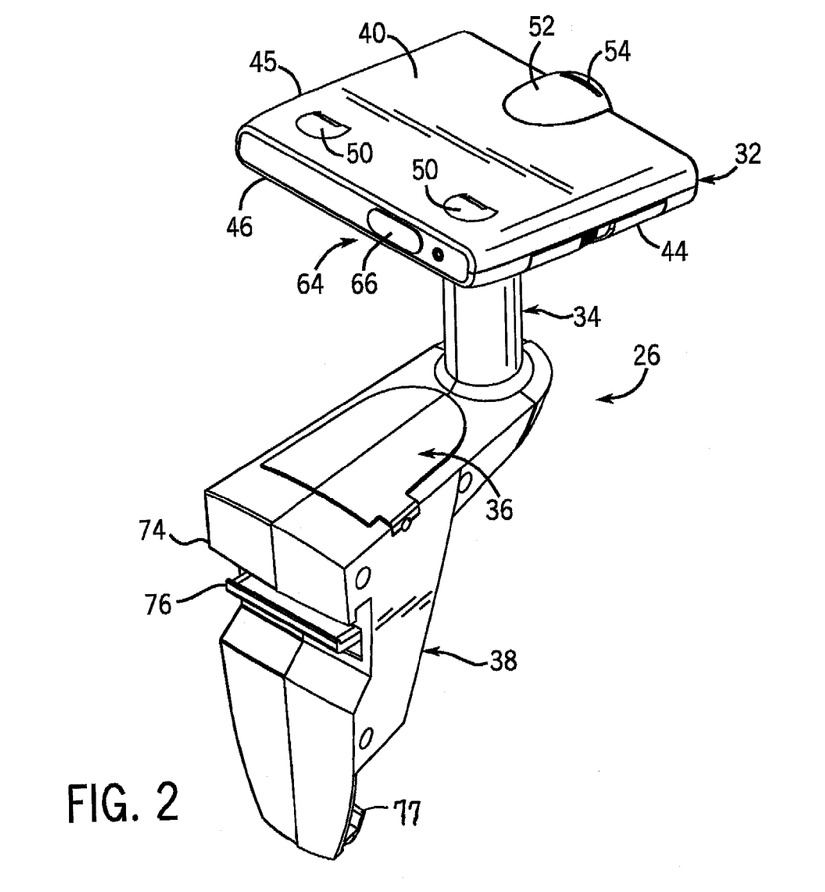
FIG. 2 is a front perspective view of a mounting platter forming part of the system of FIG. 1.
Figure 3:
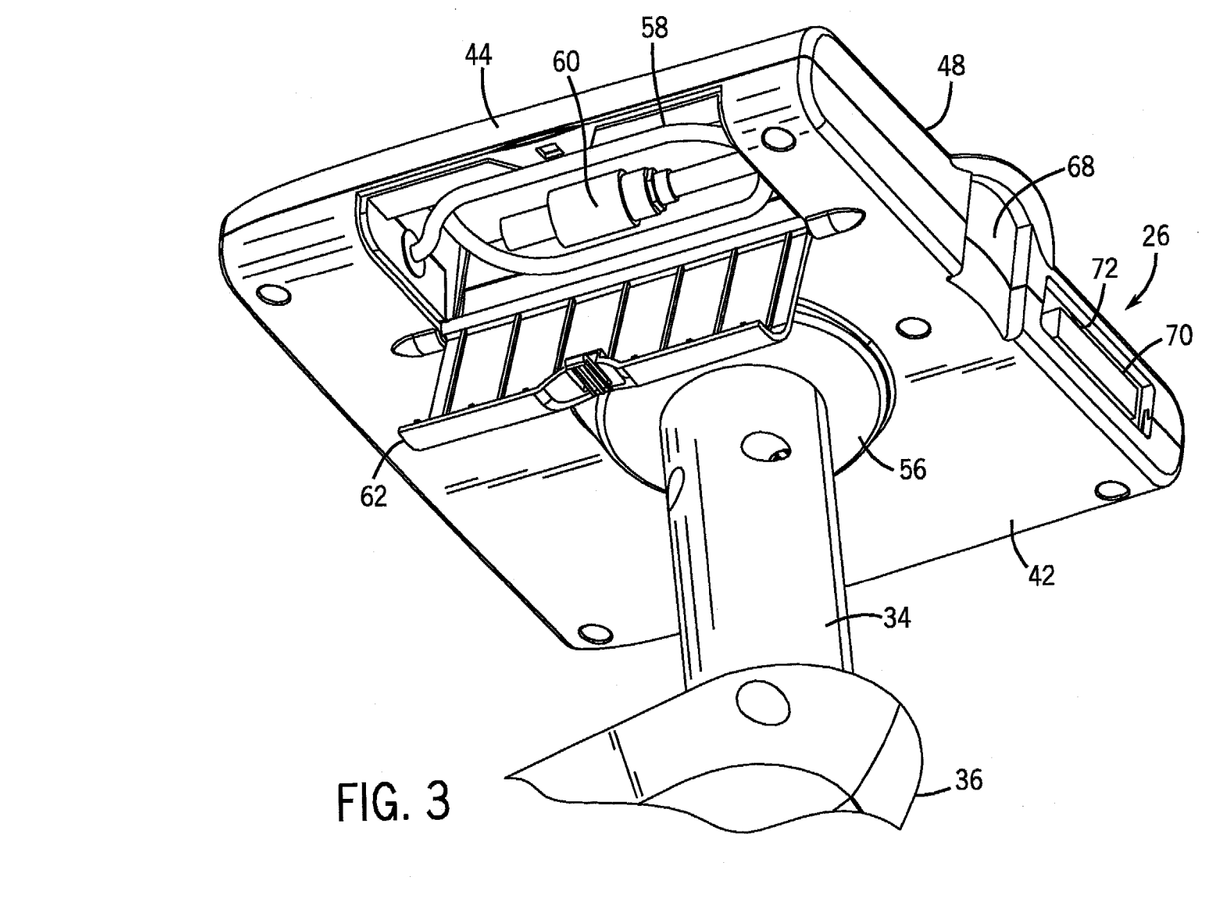
FIG. 3 is a partial bottom perspective view of the mounting platter of FIG. 2.

Referring now to FIGS. 2 and 3, the mounting arrangement 26 includes a mounting deck or platter 32, a vertical spindle 34, an offset extension 36 and an attachment bracket 38. The mounting platter 32 has a top surface 40, a bottom surface 42, opposite side surfaces 44, 45, a front surface 46 and a rear surface 48. The top surface 40 is formed on its forward end with a pair of spaced apart raised shoes 50, as more clearly depicted in FIG. 2. At the center rear end of the top surface 40 is a raised dome 52 having a portion which extends slightly beyond the rear surface and is formed with a slot 54 therethrough. As will be understood hereafter, the shoes 50 and slotted dome 52 serve as alignment and locking devices for securing at least one catheter module 28 to the mounting platter 32 in superposed relationship.

Figure 7:
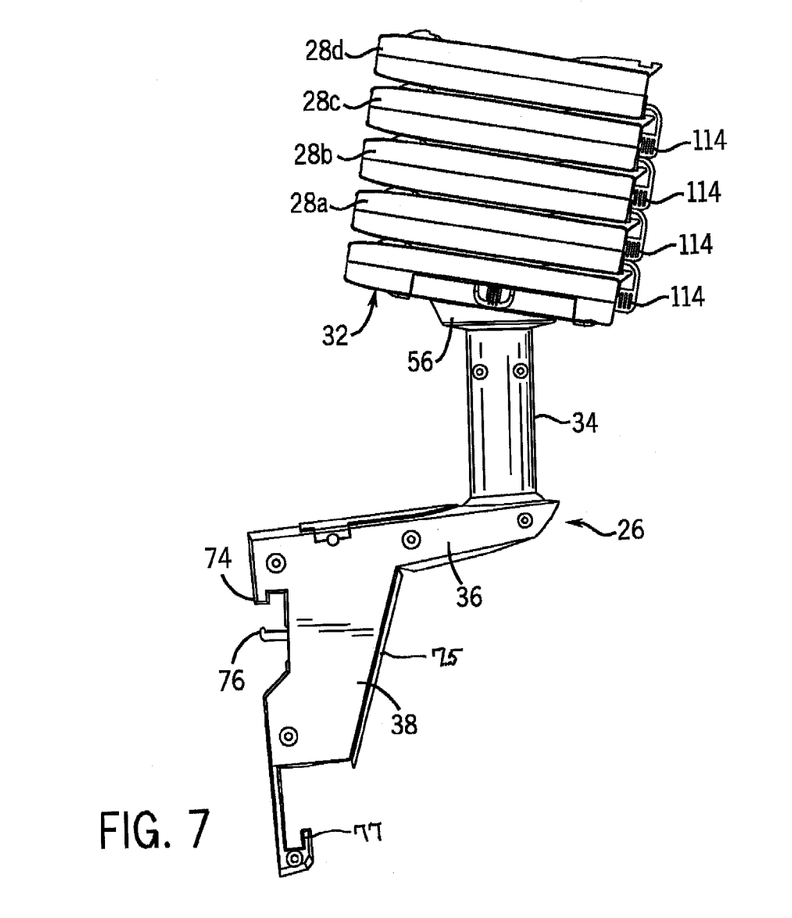
FIG. 7 is a side view of a series of stacked catheter input devices electrically and mechanically coupled to the mounting platter.

As seen best in FIGS. 3 and 7, the bottom surface 42 has an annular understructure 56 for receiving an upper end of the spindle 34 such that the mounting platter 32 will be rotatable relative to the spindle 34. The lower end of the spindle 34 is fixed on one end of the extension 36 which is integrally secured to the attachment bracket 38 that is conveniently designed to be movably attached to a bed rail 14. The understructure 56 on the bottom surface 42 of the mounting platter 32 permits approximately 200 degrees of rotation of the mounting platter 32 relative to the conjoined spindle 34, extension 36 and attachment bracket 38 secured to the bed 12. The understructure 56 further is constructed to angularly orient the mounting platter 32 so that the front surface 46 is tilted slightly upwardly. The bottom surface 42 and part of the side surface 44 are formed with a compartment 58 for retaining a simulator cable 60 that can be accessed and used to check a bad catheter or system malfunction during EP and HEMO studies. A cover 62 is normally snap fit in place over the compartment 58 to conceal and protect the cable 60. The cover 62 is pivotally secured to the bottom surface 42 and may be released to provide access to the compartment 58 if desired.

The front surface 46 of the mounting platter 32 is formed with various input structure 64, a portion of which is covered by a removable cap 66. The input structure 66 functions, in part, to enable communication with one end of the simulator cable 60. The rear surface 48 is configured with a central channel 68 which is aligned with the slot 54 in the dome 52 on the top surface 40. The rear surface 48 also features an electrical connector 70 that projects outwardly from a recess 72 on one side of the channel 68.

As shown in FIGS. 2 and 7, the attachment structure 38 on the mounting bracket 26 includes a first hook 74 and a pivoting jaw 76 which together define a clamping arrangement that is frictionally retained on and slidably supported along the bed rail 14. An actuating handle 75 is pivotally mounted to attachment structure 38 and operably connected to pivoting jaw 76. Selective manual movement of handle 75 will retract and extend jaw 76 to enable clamping the mounting bracket 26 to bed rail 14. The attachment structure 38 also includes a second hook 77, which provides a suspended mounting. The spindle 34 acts as a grip or handle which can be grasped to move the mounting arrangement 26 back and forth along the bed rail 14. The hooks 74 and 77 and the jaw 76 are constructed so that the mounting arrangement 26 is supported upwardly at the patient's level or may be suspended on the bed rail 14 so as to be tucked beneath the bed 12 as represented in FIG. 1. The mounting arrangement 26 is particularly advantageous in routing a single cable 78 from the mounting platter 32 to the central processing device 30.

Figure 4:
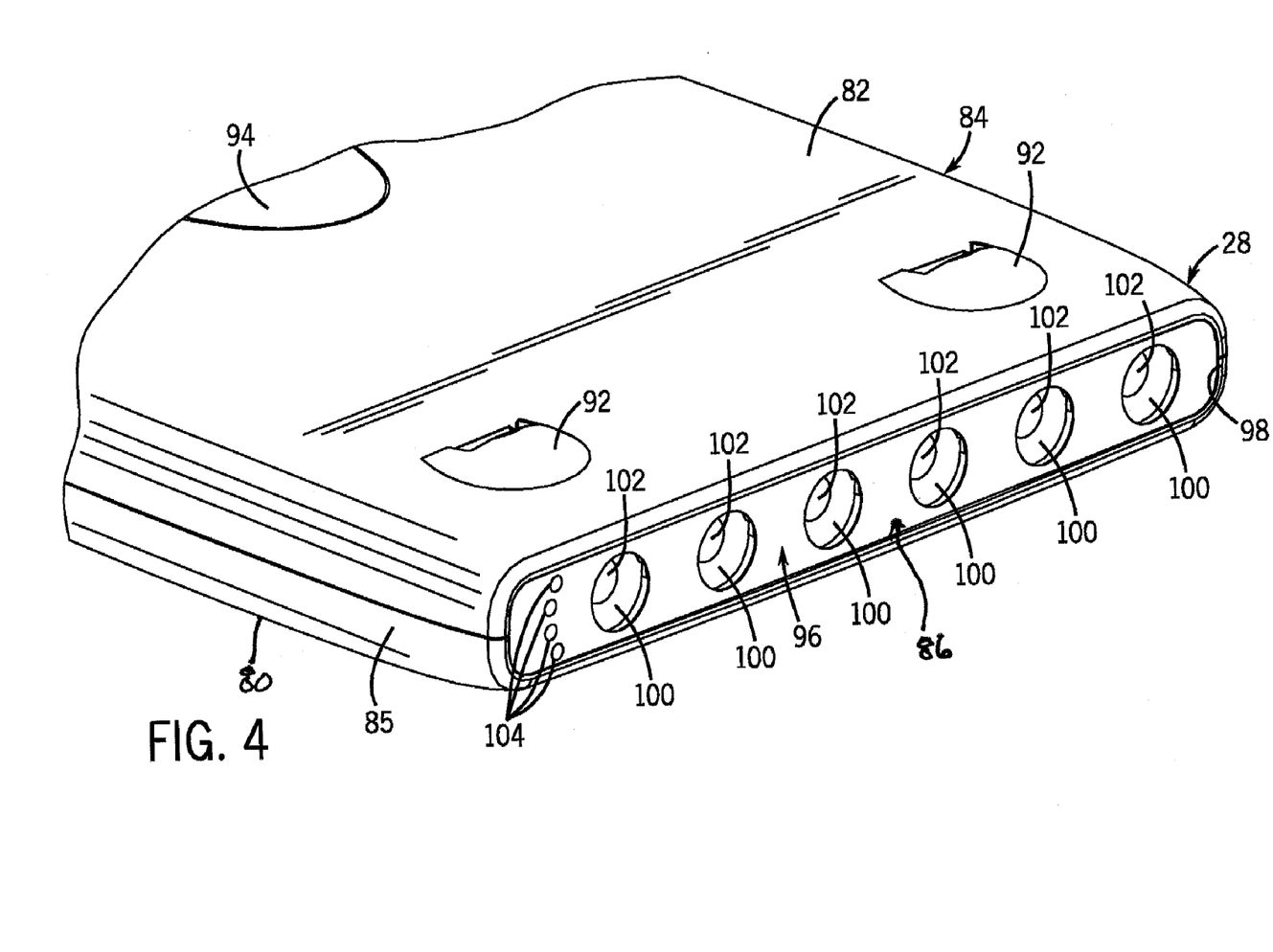
FIG. 4 is a partial front perspective view of a catheter input device forming part of the system.
Figure 5:
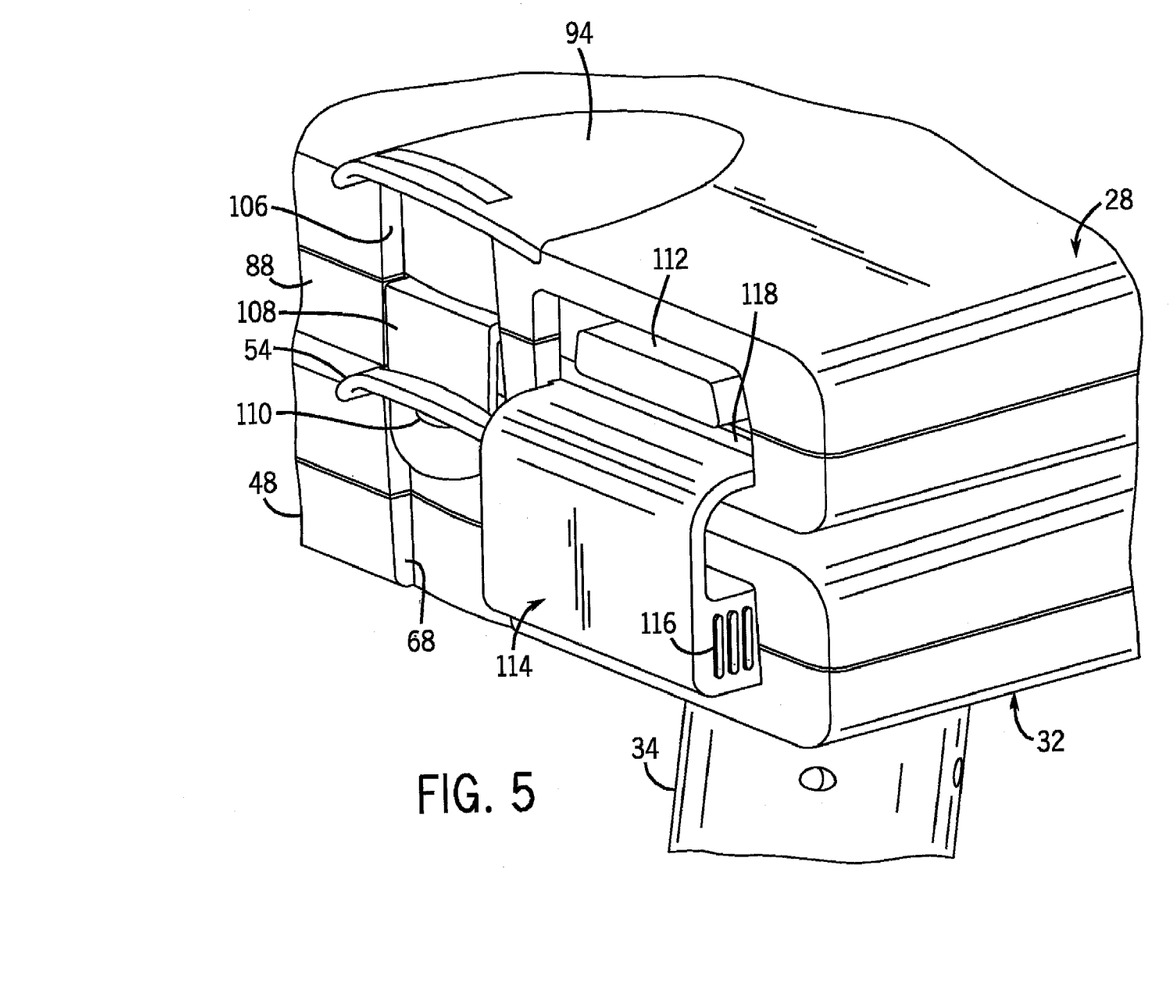
FIGS. 5 and 6 are partial rear perspective views of the mounting platter of FIG. 2 electrically coupled to a single computer input device.
Figure 8:
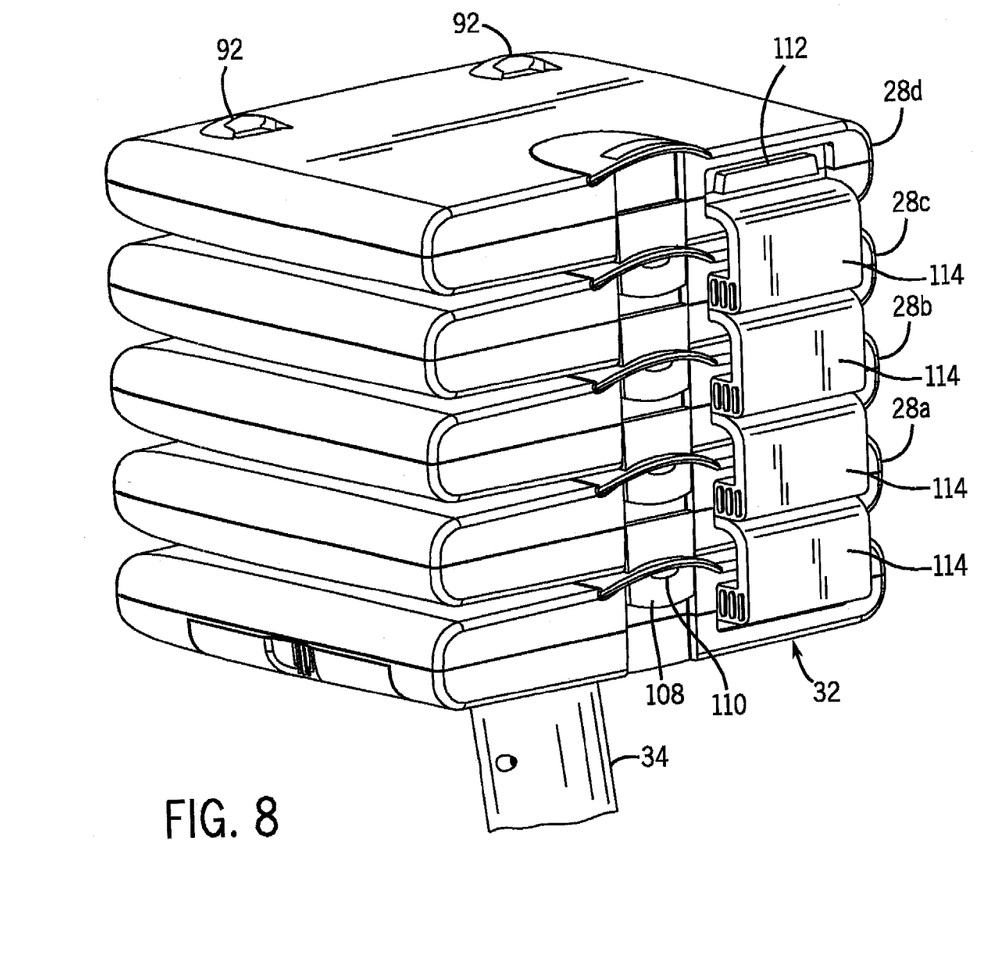
FIG. 8 is a partial rear view of FIG. 6.
Figure 9:
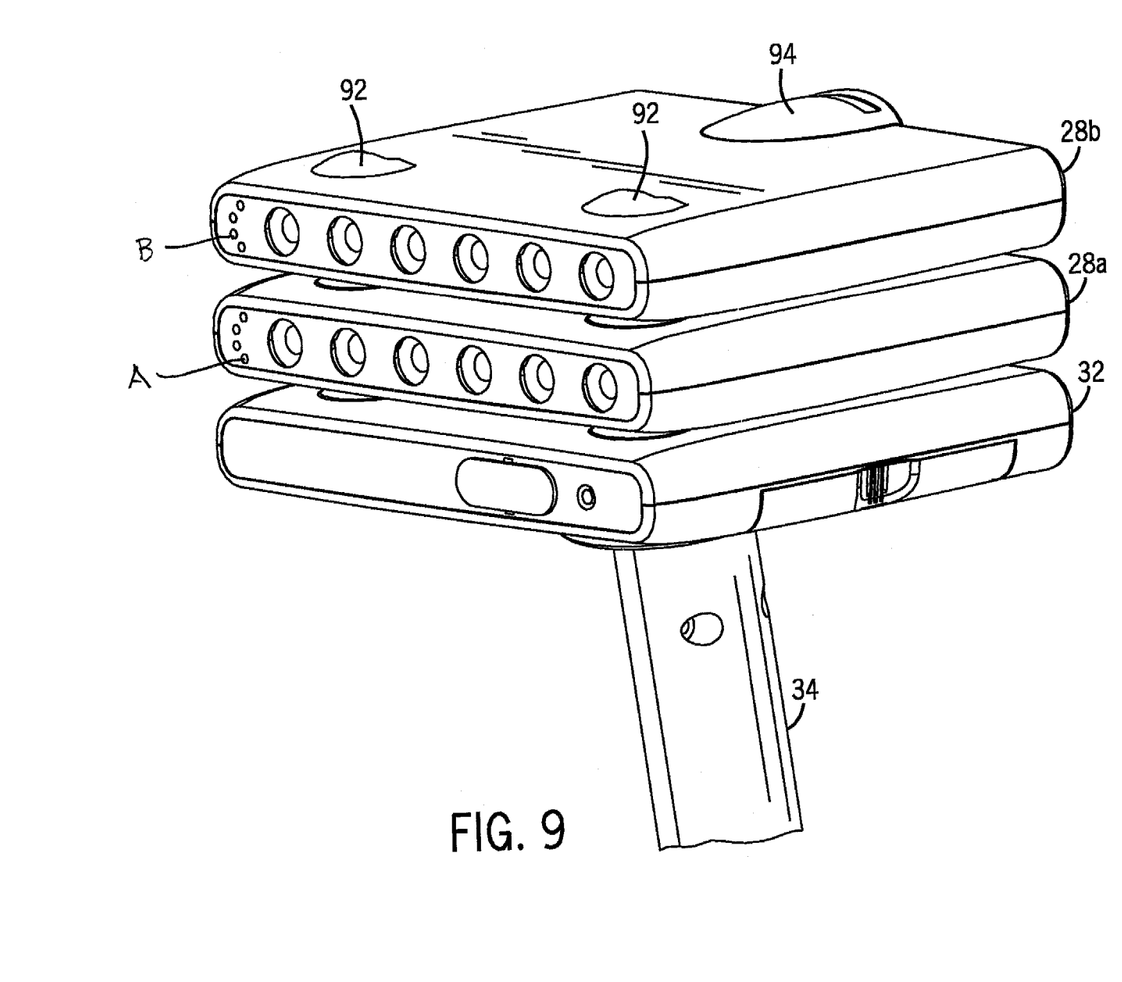
FIG. 9 is a front perspective view of two catheter input modules electrically and mechanically coupled to the mounting platter.

The mounting platter 32 functions as an electrical and mechanical foundation for at least one catheter input module 28 (FIGS. 4-6), and optionally a series of stacked identical catheter input modules 28a,b,c,d (FIGS. 7-9). Each catheter input module 28 has a bottom surface 80, a top surface 82, opposite side surfaces 84, 85, a front surface 86 and a rear surface 88. The bottom surface 80 has a pair of forwardly disposed, spaced apart feet (not shown) that are aligned and engaged with the shoes 50 on the top surface 40 of mounting platter 32. The bottom surface 80 of the module 28 also has a cored out section (not shown) centrally located on a rear portion. This section is aligned with and receives the dome 52 on the top surface 40 of the mounting platter 32. As seen in FIGS. 4 and 5, the top surface 82 of each module 28 has feet 92 and a slotted dome construction 94 constructed and located similarly to those on the top surface 40 of the mounting platter 32.

The front surface 86 is provided with a removable cover 96 which is friction fit in a recess 98 formed at the front of the module 28. The cover 96 is formed with a number of spaced apart circular openings 100 in register with and connected to an equal number of electrical connectors 102. The jacks 24 on the catheter wires 22 are inserted into openings 100 and plugged into the connectors 102 so that data may be transmitted from the patient through the catheters 20 to the module (s) 28. As pictured in FIG. 4, the cover 96 includes a set of LEDs 104 which are appropriately labeled such as with indicia (A,B,C,D) to signify the maximum number of modules 28 which may be stacked together one on top of the other. The LEDs 104 are powered by means of electrical contact with suitable structure in the module 28 behind the cover 96, and are tied to the system software to identify and recognize a particular module 28 when it has been properly coupled to the mounting platter 32 or another module 28 as will be further discussed below.

Figure 6:
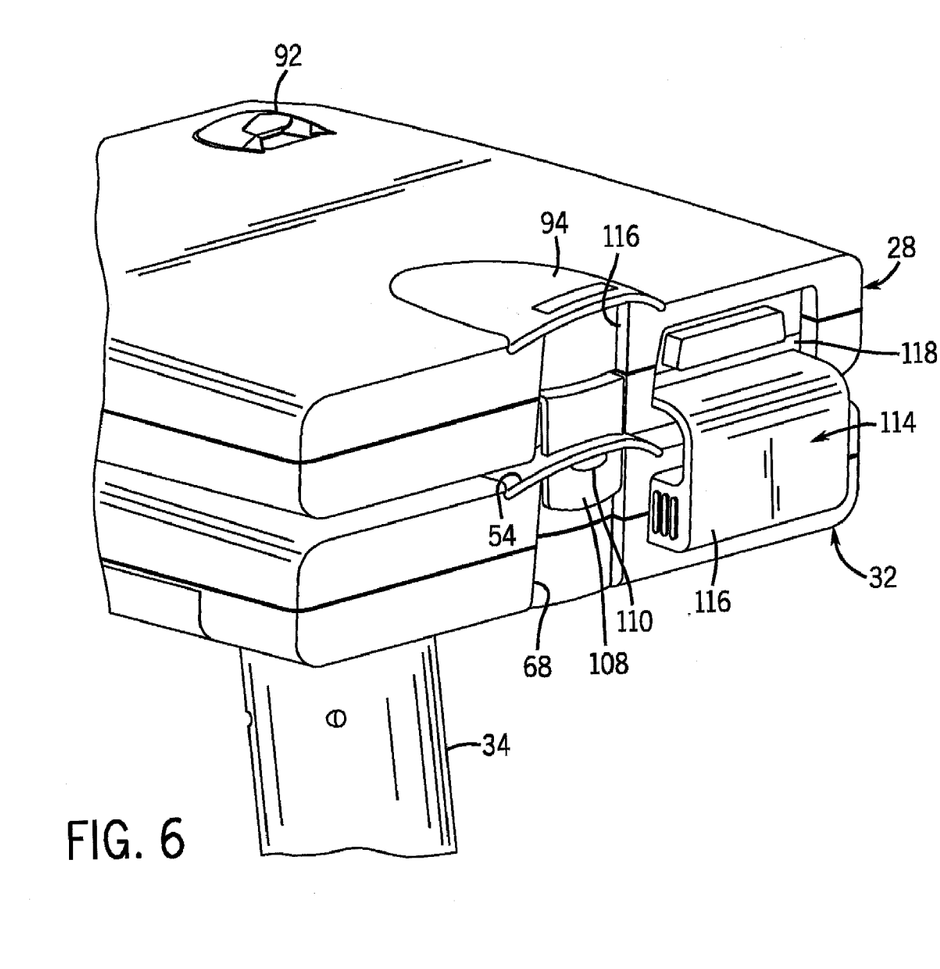

Referring to FIGS. 5 and 6, the rear surface 88 of each module 28 includes a channel 106 similar to and aligned with channel 68 formed in the mounting platter 32. A tongue 108 having a raised portion on ramp 110 is hingedly attached to the sidewalls forming the channel 106. The tongue 108 and the ramp 110 are inserted through the slot 54 in the dome 52 of the mounting plate 32 until the ramp 110 snaps beneath an underside of the dome extension and the tongue 108 extends into the mounting platter channel 68. The ramped tongue 108 and slot 54 thus define a latching arrangement for holding the module 28 upon the mounting platter 32. Because of the latching arrangement and the alignment and locking between the shoes 50 and the feet on the top surface 40 of the mounting platter 32 and the bottom surface 80 of the module 28, the mounting platter 32 and module 28 are positively mechanically locked together and restrained in six degrees of freedom. Forcing the ramped tongue 108 upwardly through the slot 54 will permit mechanical uncoupling of the module 28 from the mounting platter 32. Additional modules 28a,b,c,d may be mechanically locked together in the same manner as described so as to form the stacked formation illustrated in FIGS. 7, 8 and 9.

A rear surface 88 of each module 28 also includes an electrical connector 112 that extends rearwardly from a recess 114 provided on one side of the module channel 106. Beneath the electrical connector 112 is an opening (not shown) which is in communication with a circuit board (not shown) retained inside the module 28. A harness 114 having an internal ribbon cable has a lower end 116 which is coupled to the mounting platter electrical connector 70. The harness 114 has an upper end 118 which extends into the opening for engagement with the circuit board so that the mounting platter 32 and the module 28 are electrically coupled together. Additional modules 28 may be electrically connected together in a similar manner as shown in FIGS. 7 and 8. The harnesses 114 thus create a "daisy-chain" electrical connection of the modules 28 and the mounting platter 32.

Figure 10:
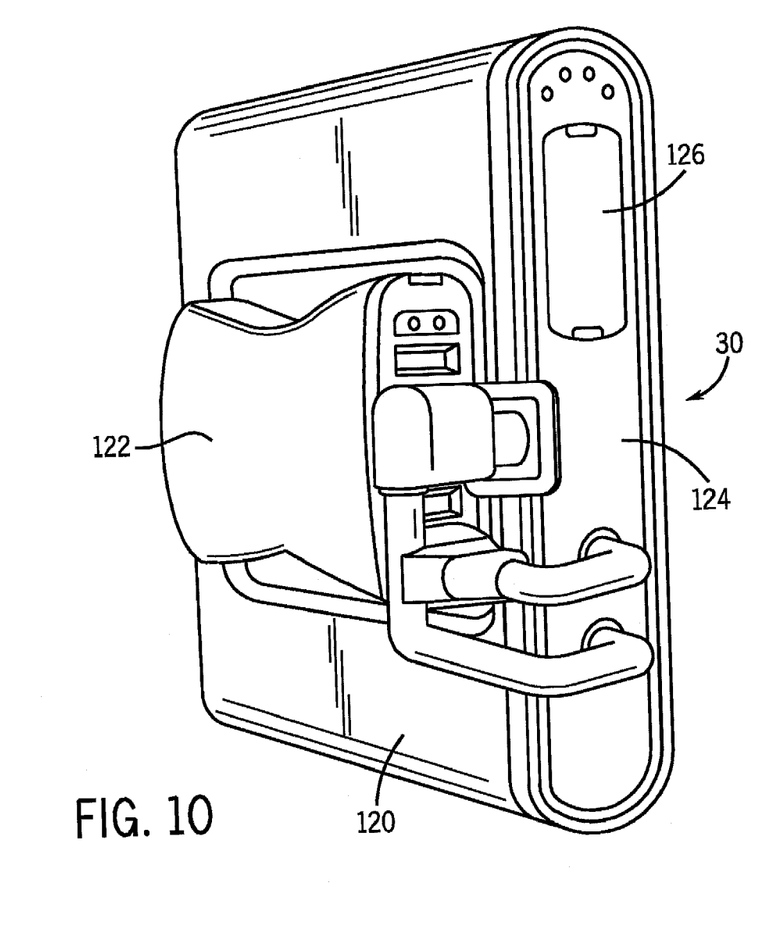
FIG. 10 is a front perspective view of a base forming part of the system.

With attention to FIGS. 1 and 10, the central processing device 30 is removably secured to the pedestal 16 beneath the bed 12, and includes a base 120 having a detachable acquisition module 122 for receiving vital statistics patient data. The base 120 has a front panel 124 with a removable cap 126 containing various inputs. A rear panel (not shown) also has suitable inputs. The base 120 is integrated together with the acquisition module 122 so that it can be used in both EP and HEMO studies. The base 120 is normally connected to a computer (not shown) and is also connected by the single cable 78 to the mounting platter 32 as above stated.

In use, the mounting arrangement 26 is clamped to the bed rail 14 and connected to the central processing device 30 installed on bed pedestal 16 at a position which is located outside the sterile field of the patient. One or more catheter input modules 28 are then mechanically and electrically coupled to the mounting platter 32 as described previously. With the desired number of modules 28 in place, the jacks 24 from the various catheters 20 are plugged into the appropriate modules. When each module 28 has been properly electrically connected, a single dedicated LED 104 corresponding to that particular module 128 will be illuminated signifying module identification and recognition by the system software. For example, in the stacked formation of FIG. 9, module 28a will show LED "A" illuminated and module 28b will show LED "B" illuminated. With the mounting arrangement 26, the catheter input module(s) 28 and the central processing device 30 properly coupled together, either an EP or HEMO study may proceed.

The present invention thus provides a convenient versatile and unified electromechanical coupling system 10 which may be utilized in both EP and hemodynamic studies. The system 10 eliminates the problem of a jungle of wires extending from catheter input modules separately located adjacent the patient and leading into a large, floor-mounted central processing device. In contrast, the present invention provides for integrated cable management thereby solving the clutter and noise problems which have occurred in the past. The system 10 also efficiently provides for room-to-room portability and enables a stacked formation of catheter input modules 28 to be slidably mounted on a bed 12 and positioned at different levels relative to the bed. In addition, the mounting arrangement 26 permits an angular presentation and a rotation of the module(s) 28 which allows medical personnel on either side of the bed 12 to clearly view the front or input side of the modules(s) 28. The removable connector cover 96 and its joined connectors 102 on module 28 may be replaced when desired due to an accumulation of foreign matter thereby preventing the costly replacement of an entire module 28. The central processing device 30 is uniquely designed for use with both EP and HEMO studies, and is connected to both the mounting platter 32 and the system computer with minimal cabling.

While the invention has been described with reference to a preferred embodiment, those skilled in the art will appreciate that certain substitutions, alterations and omissions may be made without departing from the spirit thereof. Accordingly, the foregoing description is meant to be exemplary only and should not be deemed limitative on the scope of the invention set forth with the following claims.

We claim:

1. An electro-mechanical system used in combination with at least one catheter in performing a medical diagnostic procedure on a patient situated on a support structure, comprising:
   a mounting arrangement configured to be coupled to the support structure for sustaining the patient, wherein the mounting arrangement extends either above or below the patient support structure;
   at least one catheter input module mechanically coupled to the mounting arrangement, the catheter input module being connected in communication with the at least one catheter; and
   a central processing device mechanically coupled at the support surface structure and connected in communication with the at least one catheter input module,
   wherein the mounting arrangement has an attachment structure that is removably coupled by a snap fit connector frictionally retained and slidably supported on the support structure without the need for manually tightening and loosening the attachment structure to the support structure.

2. The system of claim 1, wherein the mounting arrangement and the catheter input module have a cooperating alignment and a cooperating locking structure.

3. The system of claim 1, wherein a plurality of catheter input modules are electrically and mechanically coupled to the mounting arrangement.

4. The system of claim 3, wherein the stacked catheter input modules and the mounting arrangement are interconnected to one another by a latching arrangement.

5. The system of claim 3, wherein the stacked catheter input modules and the mounting arrangement are electrically connected together by a harness arrangement.

6. The system of claim 1, wherein the central processing device is coupled to the mounting arrangement by a single cable.

7. The system of claim 1, wherein the mounting arrangement and the at least one catheter input module are interconnected to one another by a latching arrangement.

8. The system of claim 7, wherein the latching arrangement comprises a ramped tongue on the catheter input module and a slotted dome on the mounting arrangement.

9. The system of claim 1, wherein the mounting arrangement and the at least one catheter input module are electrically connected together by a harness having a ribbon cable.

10. The system of claim 1, wherein the at least one catheter input module has a removable cover formed with openings and secured to connectors for receiving input jacks of catheters.

11. The system of claim 10, wherein the removable cover is provided with an LED arrangement for verifying the electrical coupling of the mounting arrangement to the at least one catheter input module.

12. The system of claim 1, wherein the mounting arrangement includes a mounting platter rotatably attached to a top end of a vertical spindle, and an offset extension with an attachment bracket fixed to a lower end of the spindle.

13. The system of claim 12, wherein a top surface of the mounting platter comprises elements that are configured to align with and engage apertures formed on a bottom surface of the at least one catheter input module.

14. The system of claim 12, wherein a top surface of the mounting platter is provided with a slotted dome that is aligned with and received in an open portion formed on a surface of the catheter input module.

15. The system of claim 12, wherein surfaces of the mounting platter and the catheter input module are formed with projecting electrical connectors that are configured to couple together.

16. The system of claim 1, wherein the central processing device includes a base attachable to the support structure and an acquisition module coupled to the base.

17. The system of claim 1, wherein the central processing device is configured to be used in both electrophysiology and hemodynamic studies.

18. In a patient monitoring system used in combination with at least one catheter in performing an electrophysiology study of a patient positioned on a support structure, comprising:
- a plurality of catheter input modules connected in communication with the at least one catheter;
- a central processing device connected in communication with the plurality of catheter input modules; and
- a mounting arrangement movably coupled to the support structure such that the mounting arrangement extends either above or below the patient support structure;
- wherein the plurality catheter input modules are mechanically connected to each other and the mounting arrangement in a stacked formation by a latching and alignment arrangement, and
- wherein the central processing device is configured to removably attach to the support structure and is configured to electrically connect to the mounting arrangement by a single cable.

* * * * *